(12) United States Patent
Sumanasinghe

(10) Patent No.: US 11,786,388 B2
(45) Date of Patent: Oct. 17, 2023

(54) ENDOVASCULAR DELIVERY SYSTEMS WITH RADIAL ORIENTATION MECHANISMS

(71) Applicant: COOK MEDICAL TECHNOLOGIES LLC, Bloomington, IN (US)

(72) Inventor: Ruwan Sumanasinghe, Carmel, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 0 days.

(21) Appl. No.: 17/200,075

(22) Filed: Mar. 12, 2021

(65) Prior Publication Data
US 2022/0287860 A1 Sep. 15, 2022

(51) Int. Cl.
*A61F 2/962* (2013.01)
*A61F 2/95* (2013.01)
*A61F 2/24* (2006.01)

(52) U.S. Cl.
CPC .............. *A61F 2/962* (2013.01); *A61F 2/243* (2013.01); *A61F 2002/9505* (2013.01); *A61F 2002/9511* (2013.01)

(58) Field of Classification Search
CPC .............. A61F 2/962; A61F 2002/9505; A61F 2002/9511; A61F 2/243
See application file for complete search history.

(56) References Cited

U.S. PATENT DOCUMENTS 3,517,128 A * 6/1970 Hines ................... A61M 29/02
606/198
4,585,000 A * 4/1986 Hershenson .......... A61M 29/02
604/109
(Continued)

FOREIGN PATENT DOCUMENTS

CN 207562016 U 7/2018
EP 0330376 A2 8/1989
(Continued)

OTHER PUBLICATIONS

Partial European Search Report in Related European Case No. 22275015.0 dated Aug. 29, 2022 (15 pages).

*Primary Examiner* — Jing Rui Ou
(74) *Attorney, Agent, or Firm* — Crowell & Moring LLP

(57) ABSTRACT

The present embodiments provide delivery systems for facilitating orientation of a prosthesis in a bodily passage. In one example, a system comprises an inner cannula having proximal and distal regions, and further comprises an atraumatic tip having a proximal end, a distal end, and a central region disposed therebetween. At least a portion of the atraumatic tip may be coupled to the proximal region of the inner cannula. A plurality of orientation struts are provided having a retracted delivery state, an expanded deployed state, and a retracted withdrawal state. The plurality of orientation struts each have apices that are oriented proximally relative to the atraumatic tip in the retracted delivery state, are oriented radially outward relative to the atraumatic tip in the expanded deployed state, and are oriented distally relative to the atraumatic tip in the retracted withdrawal state.

16 Claims, 10 Drawing Sheets

(56) References Cited

U.S. PATENT DOCUMENTS

| | | | |
|---|---|---|---|
| 5,443,477 A * | 8/1995 | Marin | A61F 2/95 606/198 |
| 5,713,907 A * | 2/1998 | Hogendijk | A61M 29/02 606/198 |
| 5,971,938 A | 10/1999 | Hart et al. | |
| 6,468,298 B1 * | 10/2002 | Pelton | A61F 2/95 606/198 |
| 7,306,617 B2 | 12/2007 | Majercak | |
| 8,652,193 B2 | 2/2014 | Dorn | |
| 9,056,008 B2 | 6/2015 | Righini et al. | |
| 9,078,746 B2 | 7/2015 | Pavcnik et al. | |
| 9,220,617 B2 | 12/2015 | Berra | |
| 9,456,888 B2 | 10/2016 | Chin et al. | |
| 9,655,712 B2 | 5/2017 | Berra et al. | |
| 9,681,968 B2 | 6/2017 | Goetz et al. | |
| 9,713,523 B2 | 7/2017 | Zacharias et al. | |
| 9,913,743 B2 | 3/2018 | Arbefeuille et al. | |
| 9,925,080 B2 | 3/2018 | Arbefeuille et al. | |
| 9,980,840 B2 | 5/2018 | Havel et al. | |
| 2003/0050694 A1 * | 3/2003 | Yang | A61F 2/243 623/2.11 |
| 2004/0167602 A1 | 8/2004 | Fischell et al. | |
| 2005/0033406 A1 | 2/2005 | Barnhart et al. | |
| 2009/0230169 A1 | 9/2009 | Xiao et al. | |
| 2010/0268317 A1 | 10/2010 | Stiger et al. | |
| 2011/0054519 A1 | 3/2011 | Neuss | |
| 2014/0135899 A1 | 5/2014 | Chobotov | |
| 2014/0358215 A1 * | 12/2014 | Baylis | A61F 2/95 623/1.12 |
| 2015/0157479 A1 | 6/2015 | Parsons et al. | |
| 2015/0164667 A1 | 6/2015 | Vinluan et al. | |
| 2015/0245934 A1 | 9/2015 | Lombardi et al. | |
| 2015/0313702 A1 | 11/2015 | McGuckin et al. | |
| 2016/0045350 A1 | 2/2016 | Berra | |
| 2016/0113703 A1 | 4/2016 | Danek et al. | |
| 2016/0213470 A1 | 7/2016 | Ahlberg et al. | |
| 2016/0228681 A1 | 8/2016 | DiPalma et al. | |
| 2016/0235531 A1 | 8/2016 | Ciobanu et al. | |
| 2016/0270910 A1 | 9/2016 | Birmingham et al. | |
| 2016/0310301 A1 | 10/2016 | Moore et al. | |
| 2016/0310303 A1 | 10/2016 | Thapliyal | |
| 2017/0100232 A1 | 4/2017 | Arbefeuille et al. | |
| 2017/0128704 A1 | 5/2017 | Lenihan et al. | |
| 2017/0303927 A1 | 10/2017 | Dickinson et al. | |
| 2018/0028191 A1 | 2/2018 | Bradway et al. | |
| 2018/0036124 A1 | 2/2018 | Tran et al. | |
| 2018/0110610 A1 | 4/2018 | Kolbel et al. | |
| 2018/0110638 A1 | 4/2018 | Berra et al. | |
| 2018/0125688 A1 | 5/2018 | Chambers | |
| 2018/0140418 A1 | 5/2018 | Sandhu et al. | |
| 2018/0235788 A1 | 8/2018 | Hyodoh et al. | |
| 2018/0250136 A1 | 9/2018 | Linder-Ganz et al. | |
| 2021/0069468 A1 | 3/2021 | Keating et al. | |

FOREIGN PATENT DOCUMENTS

| | | |
|---|---|---|
| EP | 2630933 | 8/2013 |
| EP | 3009102 | 1/2018 |
| ES | 2663147 T3 | 4/2018 |
| WO | WO1999/051165 | 10/1999 |
| WO | WO 2005/002660 A1 | 1/2005 |
| WO | WO 2007/059018 A2 | 5/2007 |
| WO | WO2013/118352 | 8/2013 |
| WO | WO2013/118362 | 8/2013 |

* cited by examiner

FIG. 3
FIG. 4
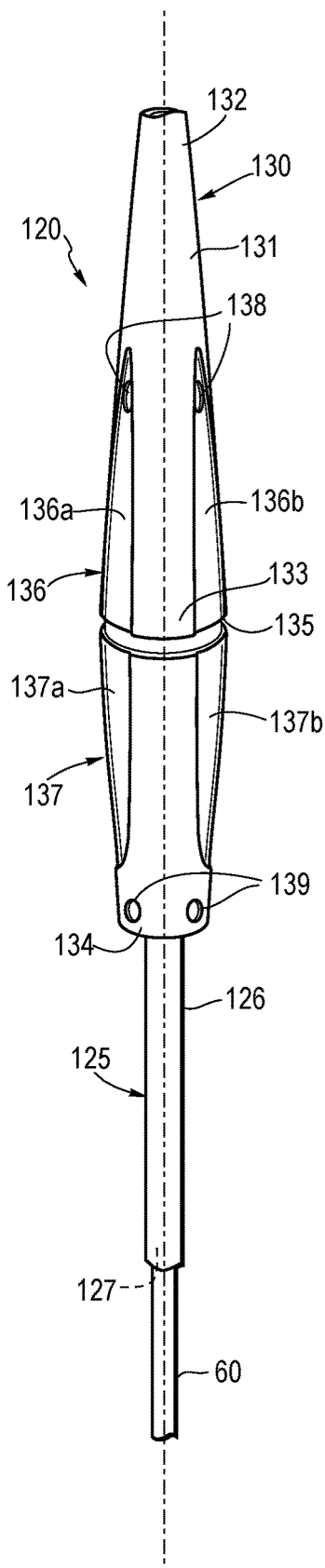
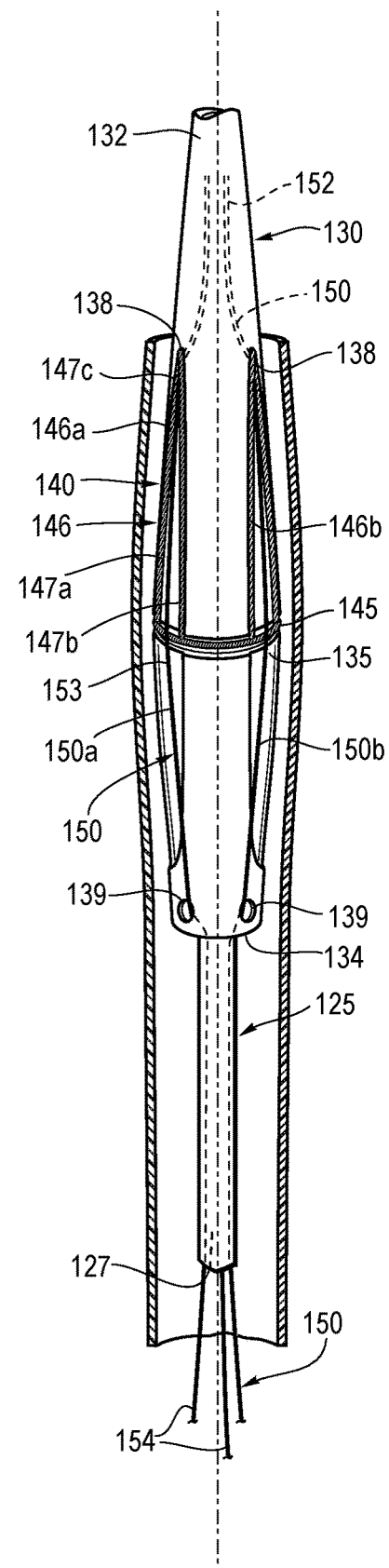

ENDOVASCULAR DELIVERY SYSTEMS WITH RADIAL ORIENTATION MECHANISMS

BACKGROUND

The present embodiments relate generally to apparatus and methods for treating medical conditions, and more specifically, to endovascular delivery systems with radial orientation mechanisms that may facilitate improved deployment of prostheses, such as stents or stent-grafts.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally beyond an edge of the graft, e.g., in order to engage a healthy portion of a vessel wall beyond a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter. Trigger wires also may be used in conjunction with different stent designs, such as cannula-cut stents having acute or pointed bends. In the latter embodiment, the trigger wires may be looped around one or more vertices formed beneath the proximal and/or distal apices, e.g., a location where an individual apex splits into two separate strut segments.

In some situations, the delivery system may not be substantially centered in a bodily passage, such as a curved vessel, and can engage a vessel wall in the region where the stent or stent-graft is to be deployed. In such situations, withdrawal of an outer sheath to expose the stent or stent-graft may cause barbs of the stent to prematurely engage a vessel wall, whether or not a trigger wire or similar mechanism is used to hold the stent or stent-graft to the delivery system. If barbs prematurely engage a portion of the vessel wall, before final positioning is confirmed or deployment of the stent is desired, then it may be difficult or impossible to recapture or reposition the stent or stent-graft at this time. Moreover, apposition of the stent or stent-graft to its intended deployed position may be compromised, leading to poor sealing with the vessel wall, potential endoleaks or other adverse events.

SUMMARY

In one example, a delivery system for facilitating orientation of a prosthesis in a bodily passage comprises an inner cannula having proximal and distal regions, and further comprises an atraumatic tip having a proximal end, a distal end, and a central region disposed therebetween. At least a portion of the atraumatic tip may be coupled to the proximal region of the inner cannula. A plurality of orientation struts are provided having a retracted delivery state, an expanded deployed state, and a retracted withdrawal state. The plurality of orientation struts each have apices that are oriented proximally relative to the atraumatic tip in the retracted delivery state, are oriented radially outward relative to the atraumatic tip in the expanded deployed state, and are oriented distally relative to the atraumatic tip in the retracted withdrawal state.

In one example, a first actuation wire of a plurality of actuation wires causes movement of a first orientation strut from the retracted delivery state, to the expanded deployed state, and to the retracted withdrawal state of the first orientation strut. A second actuation wire of the plurality of actuation wires causes movement of a second orientation strut from the retracted delivery state, to the expanded deployed state, and to the retracted withdrawal state of the second orientation strut. The first and second actuation wires may be capable of independent retraction relative to one another along their lengths, such that the first and second orientation struts may be actuated independently at different times.

In other embodiments, a delivery system for facilitating orientation of a prosthesis in a bodily passage comprises an inner cannula having proximal and distal regions, and further comprises an atraumatic tip having a proximal end, a distal end, and a central region disposed therebetween. At least a portion of the atraumatic tip may be coupled to the proximal region of the inner cannula. A plurality of axial slots extend through the central region of the atraumatic tip. A plurality of orientation struts are provided having a retracted delivery state, an expanded deployed state, and a retracted withdrawal state. Each of the plurality of orientation struts remains within the axial slots in the retracted delivery state and the retracted withdrawal state, and each of the plurality of orientation struts has a central portion extending radially outward through a respective one of the axial slots in the expanded deployed state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 3 is a side view of a delivery system having an atraumatic tip according to one embodiment, with orientation struts removed for illustrative purposes.

FIG. 4 is a side view of the delivery system of FIG. 3 showing orientation struts in a retracted delivery state.

DETAILED DESCRIPTION OF THE PREFERRED EMBODIMENTS

In the present application, the term "proximal end" is used when referring to that end of a medical device closest to the heart after placement in the human body of the patient, and may also be referred to as the inflow end (the end that receives fluid first), and the term "distal end" is used when referring to that end opposite the proximal end, or the one farther from the heart after its placement, and may also be referred to as the outflow end (that end from which fluid exits).

Figure 1A:
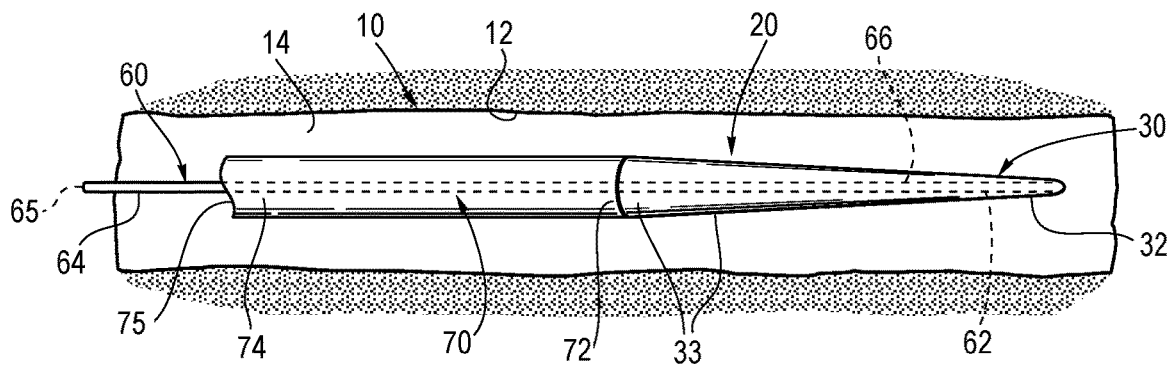
FIGS. 1A-1C are, respectively, side schematic views of a segment of a delivery system in a generally straight vessel where a proximal region of the delivery system is spaced from an inner wall of the vessel, in a generally straight vessel where the proximal region of the delivery system touches the inner wall of the vessel, and in a generally curved vessel where the proximal region of the delivery system touches the inner wall of the vessel.
Figure 1B:
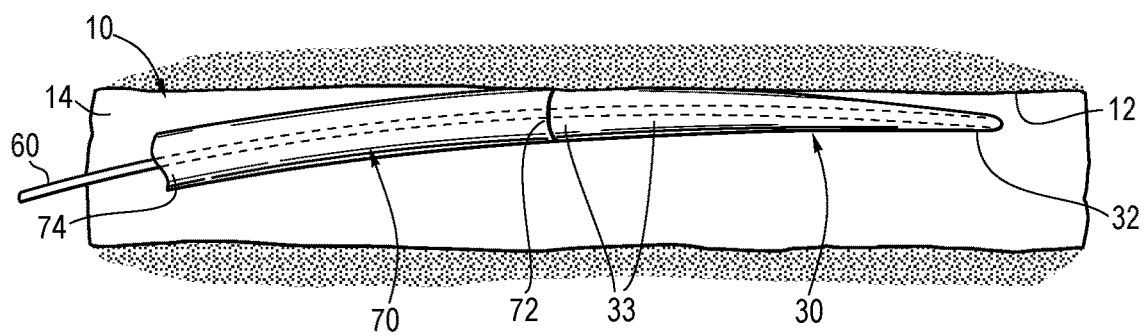
Figure 1C:
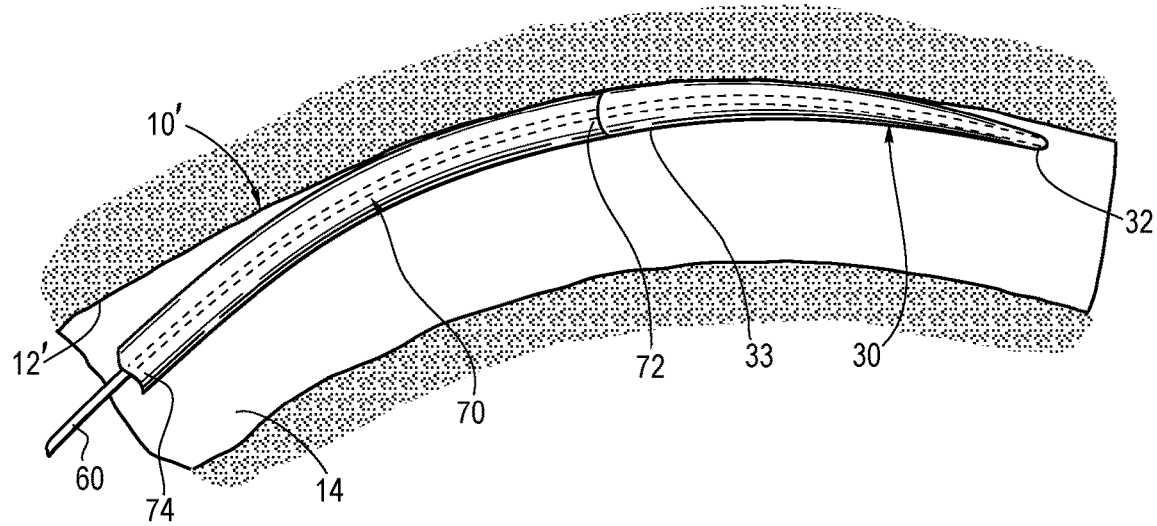

Referring to FIGS. 1A-1C, an example of a portion of a delivery system 20 having an atraumatic tip 30 is disposed within a lumen 14 of a vessel 10. The atraumatic tip 30 has a proximal end 32 (i.e., the end that receives fluid first, when disposed in an artery for example), a distal end (not visible in FIG. 1A, but comparable to distal end 134 in FIG. 3), and a central region 33 disposed therebetween. The atraumatic tip 30 tapers from a larger diameter along the central region 33 to a smaller diameter at the proximal end 32, which allows for relatively atraumatic advancement of the tip 30 in a proximal direction (left to right on the page) within the lumen 14 of the vessel 10. The distal end of the atraumatic tip 30 is enclosed within the outer sheath 70.

The delivery system 20 further comprises an inner cannula 60 and an outer sheath 70. The inner cannula 60 comprises a tubular member having proximal and distal regions 62 and 64, respectively, and a lumen 65 extending between the proximal and distal regions 62 and 64. The lumen 65 of the inner cannula 60 is sized to allow the inner cannula 60 to be advanced over a wire guide, as will be appreciated by those skilled in the art.

The atraumatic tip 30 may be affixed to an exterior surface 66 of the proximal region 62 of the inner cannula 60, using a suitable adhesive or mechanical attachment mechanism, as depicted in FIG. 1A. The proximal end 32 of the atraumatic tip 30 may be substantially flush with a proximal end of the inner cannula 60, as depicted in FIG. 1A.

The outer sheath 70 is used to retain a prosthesis, such as stent-graft 80 depicted in FIG. 2B and explained further below, in a contracted delivery configuration. The outer sheath 70 has proximal and distal regions 72 and 74, respectively (where the distal region 74 extends back towards a user), and a lumen 75 extending therebetween. The proximal region 72 of the outer sheath 70 extends over a stent 90 of the stent-graft 80, and may terminate around the distal end or central region 33 of the atraumatic tip 30, as depicted in FIGS. 1A-1C. With the entire assembly provided as shown in FIGS. 1A-1C, the stent-graft 80 may be advanced towards a target site within a patient's vessel or duct over the wire guide.

Figure 2A:
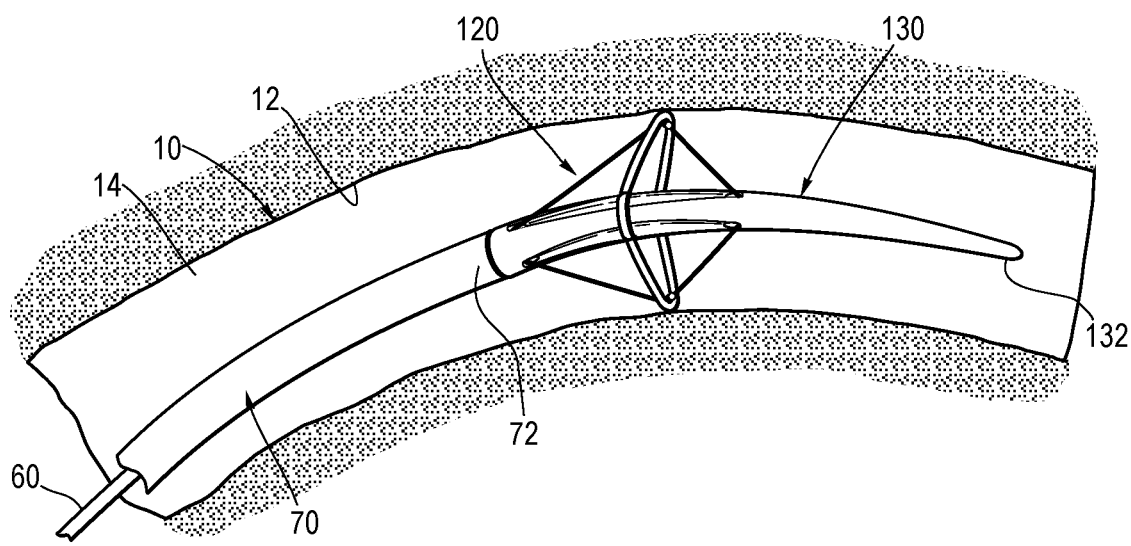
FIGS. 2A-2B are, respectively, side schematic views of a segment of a delivery system incorporating an orientation mechanism with an outer sheath in a proximal position, and the outer sheath in a distal position to expose a portion of an exemplary stent-graft.
Figure 2B:
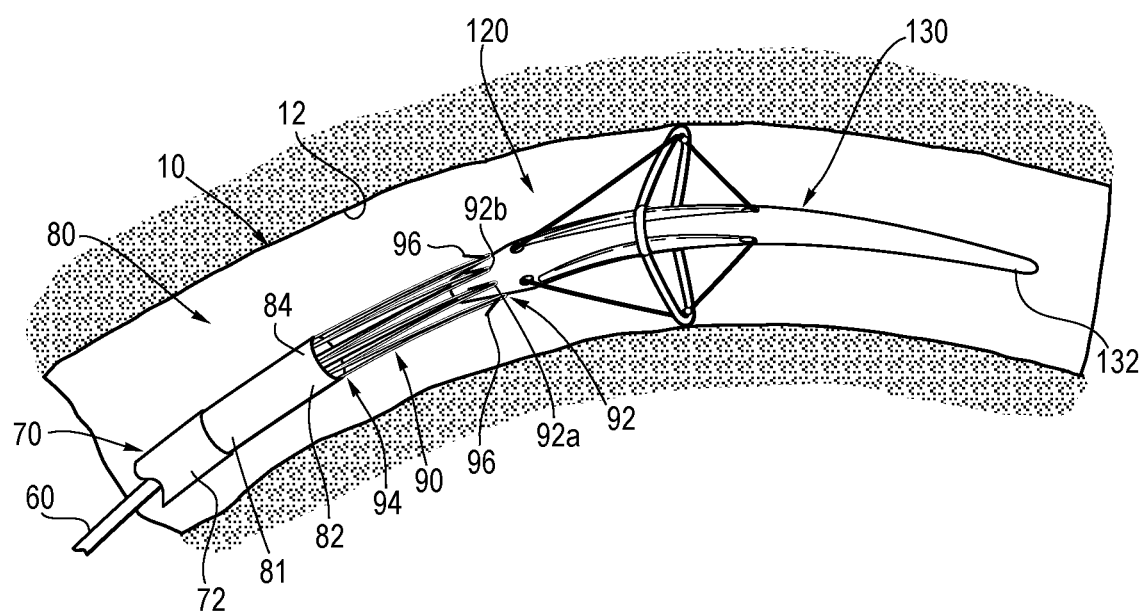

In the embodiment of FIGS. 1A-1C and FIGS. 2A-2B (and later embodiments described herein), the prosthesis may be provided, by way of one example and without limitation, according to the exemplary stent-graft 80 shown in FIG. 2B. The exemplary stent-graft 80 may comprise a stent 90 that may be manufactured into a cylindrical shape having proximal and distal ends 92 and 94, respectively. In one example, the proximal end 92 of the stent 90 may comprise multiple adjacent proximal apices 92a and 92b, as shown in FIG. 2B. In one non-limiting example, the stent 90 may be formed from a continuous cylinder into which a pattern may be cut by a laser or by chemical etching to produce slits in the wall of the cylinder. The resulting structure may then be heat set to give it a desired final configuration. The preferred final configuration includes a shape having a series of proximal apices and a series of distal apices, as generally shown in FIG. 2B. However, in an alternative embodiment, the stent 90 may be formed from one or more wires that are bent into a desired final configuration, such as a zig-zag or "Z" shape, as opposed to being formed from a laser cut cylinder, as will be appreciated by those skilled in the art.

The stent 90 has a reduced diameter delivery state so that it may be advanced to a target location within the vessel 10 when constrained at a location between the exterior surface 66 of the inner cannula 60 and an interior surface of the outer sheath 70. The stent 90 also has an expanded deployed state to apply a radially outward force upon at least a portion of the vessel 10, e.g., to maintain patency within the vessel 10, or to hold open the lumen of a graft. In the expanded state, fluid flow is allowed through a central lumen of the stent 90.

The stent 90 may be manufactured from a super-elastic material. Solely by way of example, the super-elastic material may comprise a shape-memory alloy, such as a nickel titanium alloy (nitinol). If the stent 90 comprises a self-expanding material such as nitinol, the stent may be heat-set into the desired expanded state, whereby the stent 90 can assume a relaxed configuration in which it assumes the preconfigured first expanded inner diameter upon application of a certain cold or hot medium. Alternatively, the stent 90 may be made from other metals and alloys that allow the stent 90 to return to its original, expanded configuration upon deployment, without inducing a permanent strain on the material due to compression. Solely by way of example, the stent 90 may comprise other materials such as stainless steel, cobalt-chrome alloys, amorphous metals, tantalum, platinum, gold and titanium. The stent 90 also may be made from non-metallic materials, such as thermoplastics and other polymers.

The stent 90 may be used alone or may be coupled to a graft, such as the graft 81 of FIG. 2B. In one non-limiting example, described further below, the graft 81 may comprise a proximal region 82 guiding flow towards a distal region, and the stent 90 may be coupled to the proximal region 82. In some embodiments, the stent 90 may overlap with a proximal edge 84 of the graft 81, as depicted in FIG. 2B. If the stent 90 is coupled to the graft 81 to form a stent-graft, the stent-graft may comprise multiple additional stents (not shown) along the length of the graft 81, and those stents may comprise any variety of shapes.

One or more regions of the stent 90 may comprise one or more barbs 96, which may be formed integrally with the stent 90, e.g., by laser cutting a desired barb shape into a surface of the stent, or alternatively the one or more barbs 96 may be externally formed and secured to the stent 90 by soldering or mechanical attachment means. Once the desired barb shape is provided on the stent 90, a main body of the barb 96 may be bent in a radially outward direction with respect to the stent 90, as depicted in FIG. 2B. The angle may comprise any acute angle, or alternatively may be substantially orthogonal or obtuse. If desired, the barbs 96 may be sharpened, for example, by grinding the tip of the barb, to facilitate engagement at a target tissue site.

In the example of FIGS. 1A-1C, the atraumatic tip 30 is depicted as a generic tip that lacks a radial orientation mechanism explained in FIGS. 2-12. In the embodiments of FIG. 1A-1C, the delivery system 20 may be advanced over a wire guide, and a stent-graft (such as the stent-graft 80 of FIG. 2B) is generally aligned with a region of the vessel 10 where it is desired to deploy the stent-graft. This may be performed under fluoroscopic guidance or other suitable imaging techniques. Preferably, one or more radiopaque markers are provided on the stent-graft 80 or delivery system to facilitate alignment within the body passage.

Upon initial alignment of the stent-graft 80, the outer sheath 70 may be distally retracted to expose a portion of the stent-graft 80. At this time, the stent 90 may partially self-expand, or may remain in its fully retracted configuration, e.g., by one or more trigger wires (not shown). In either instance, the barbs 96 of the stent-graft (depicted in FIG. 2B) are exposed within the vessel 10.

If the vessel 10 has a substantially straight segment, within which the stent-graft 80 is to be deployed, as depicted in FIG. 1A, then the atraumatic tip 30 may be spaced apart from an inner wall 12 of the vessel 10, and the barbs 96 of the stent-graft 80 may not immediately engage an inner wall 12 of the vessel 10 upon retraction of the sheath 70.

However, in the example of FIG. 1B, a scenario is depicted where the atraumatic tip 30 engages the inner wall of the vessel 10 even though the vessel 10 is relatively straight. Due to the stiffness of the outer sheath, including its non-conforming nature to vessel angulations, it is more common to have the atraumatic tip 30 to engage with the inner wall of the vessel 10 during the implantation procedure. Moreover, in FIG. 1C, a scenario is depicted where the atraumatic tip 30 engages the inner wall of the vessel 10 when the vessel 10 has a substantially curved segment.

The scenarios in FIGS. 1B-1C may arise in any vessel, e.g., partly due to the stiffness of the delivery system, but as particular examples may arise more predominantly in vessels with infrarenal or suprarenal angulations, or when angulations exist in an aneurysmal area. In some scenarios, the contact between the atraumatic tip 30 and the inner wall 12 of the vessel 10 may be due to the uneven or non-asymmetric forces that the body of the delivery device undergoes when inserted into the access vessels and abdominal aorta, which are not straight.

Problematically, if the atraumatic tip 30 of the delivery system 20 is in contact with the inner wall 12 of the vessel 10, then when the sheath 70 is initially retracted during deployment, the barbs 96 on the stent 90 may instantly attach to the inner wall 12 of the vessel 10, which may prevent the graft 81 from orienting itself in the vessel 10. This may lead to a poor apposition of the graft 81 to the inner wall 12 of the vessel 10. Moreover, this premature barb to vessel engagement may affect the apposition of the stent 90 to the inner wall 12 of the vessel 10, because the stent 90 loses its freedom to reorient within the vessel, as needed, before a final desired deployment of the stent-graft. Further, this lack of freedom for stent 90 to reorient in vessel lumen may prevent part of the barbs 96 of the stent 90 from engaging with the vessel 10. In an angulated vessel, this may also prevent the seal stent and sealing area (not shown) of the stent-graft 80 to properly contact with the vessel wall.

Such poor apposition of the graft 81 and/or the stent 90 to the inner wall 12 of the vessel 10 may cause type 1A endoleaks over time, particularly if the graft is not properly sealed to the vessel wall. In addition, since the proximal end 82 of the graft 81 is not perpendicular to the vessel wall, it can create uneven forces (both longitudinal and circumferential) on the barbs 96 and the stent 90, which may cause the stent 90 to fail over time. Still further, when the stent-graft tends to be in contact with one circumference of a vessel more than an opposing region, then the barbs in the opposing region may not engage a vessel wall. When used to treat an aneurysmal sac, it is important that such stent-graft 80 prevents blood flow into the sac using proximal and distal sealing areas that are positioned correctly, and provide sufficient radial outward force.

In the example of FIGS. 2A-2B, a different delivery system 120 comprises an atraumatic tip 130, which has a radial orientation mechanism according to the present embodiments (in this depiction of FIGS. 2A-2B, the atraumatic tip 130 is provided in accordance with the embodiment of FIGS. 3-6, details of which are provided below).

As can be seen in FIG. 2A, by having an atraumatic tip 130 that has a radial orientation mechanism, the atraumatic tip 130 is positioned at approximately a central location within the lumen 14 of the vessel 10, i.e., spaced-apart from the inner wall 12 of the vessel 10. Due to the spacing of the atraumatic tip 130 from the inner wall 12, when the proximal region 72 of the outer sheath 70 is initially retracted during deployment, as depicted in FIG. 2B, then the barbs 96 on the stent 90 will not instantly attach to the inner wall 12 of the vessel 10. Since the barbs 96 refrain from initial engagement with the inner wall 12, then a physician may further orient the graft 81 and/or the stent 90 within the vessel 10. This ability to make additional adjustments of the position of the stent-graft 80, even after the sheath 70 is retracted distally and the barbs 96 are exposed, can significantly improve final positioning and therefore apposition of both the graft 81 and the stent 90 to the inner wall 12 of the vessel 10, which may reduce the occurrence of endoleaks and other adverse events, such as blocking access to branch vessels that supply blood flow to the kidney, liver, and other organs. It should be appreciated that such advantages may be achieved even for stent-grafts that omit barbs 96, i.e., where frictional force alone is used to secure a stent-graft within a vessel.

Referring now to FIGS. 3-6, further features of a radial orientation mechanism of the delivery system 120, according to a first embodiment, are shown and described. For illustrative purposes, the sheath 70 and the stent-graft 80 are omitted in FIGS. 3-6, although they may be provided in accordance with the principles described above.

In FIG. 3, the delivery system 120 comprises the atraumatic tip 130 and the cannula 60, where the cannula 60 extends along the length of the delivery system 120 an attaches to an interior surface of a proximal end 132 of the atraumatic tip 130, similarly to described in FIG. 1A.

In this embodiment, a sleeve 125 is disposed coaxially around the cannula 60, such that in a delivery state the stent-graft 80 will be disposed radially between an outer surface 126 of the sleeve 125 and an interior surface of the sheath 70. The sleeve 125 comprises a lumen 127, which has a diameter larger than an outer surface of the cannula 60. One or more actuation wires 150 extend within the lumen 127 of the sleeve 125, i.e., in the space between the sleeve 125 and the cannula 60, as will be explained in FIGS. 4-6 below.

Figure 5A:
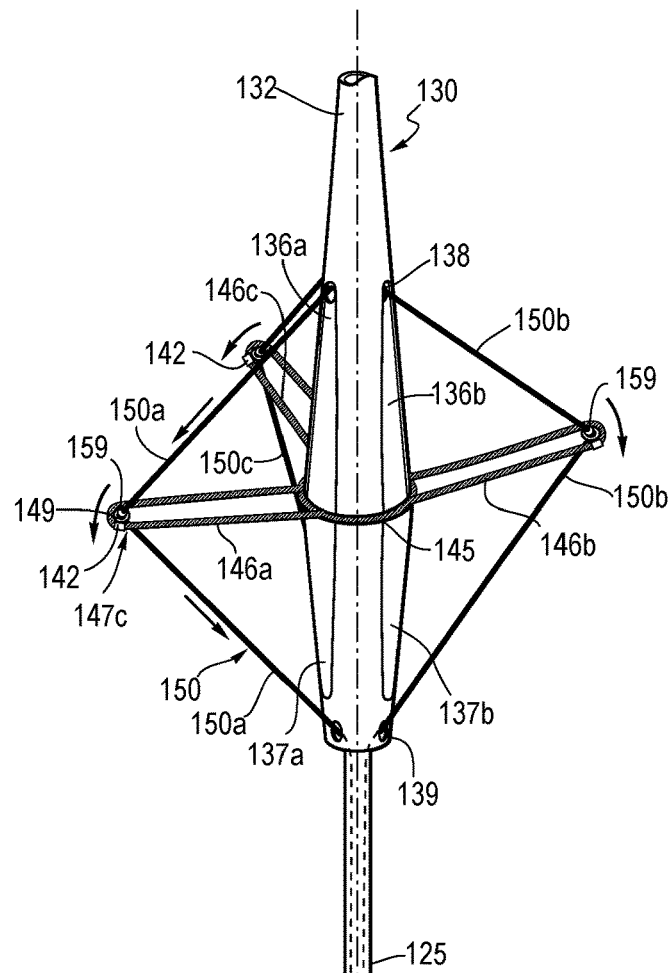
FIGS. 5A-5B are, respectively, side and top views of the delivery system of FIGS. 3-4 showing the orientation struts in an expanded deployed state.
Figure 5B:
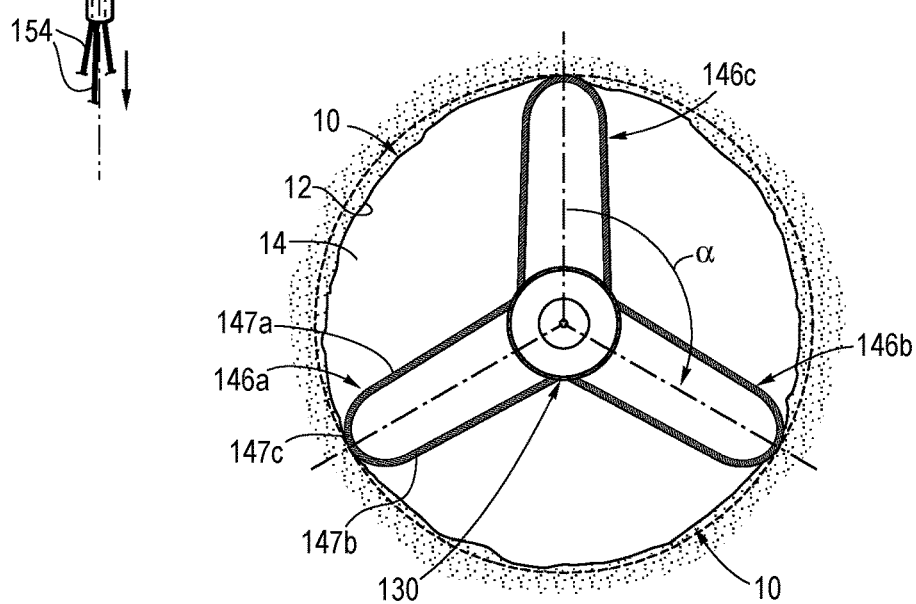
Figure 6:
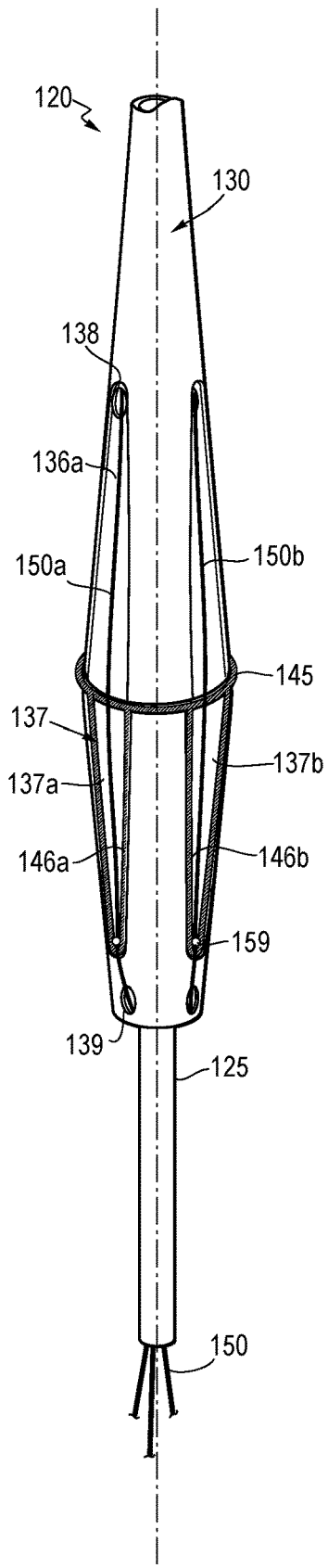
FIG. 6 is a side view of the delivery system of FIGS. 3-5 showing the orientation struts in a retracted withdrawal state.

The atraumatic tip 130 comprises various features to accommodate components of a radial orientation mechanism of FIGS. 4-6. In particular, the atraumatic tip 130 comprises a circumferential slot 135 that is recessed slightly into a main body 131 of the atraumatic tip 130, preferably near a central region 133 of the atraumatic tip 130, which may be the location of the atraumatic tip 130 with its maximum outer diameter, as generally depicted in FIG. 3. Further, one or more proximal slots 136, such as slots 136a and 136b, are also recessed slightly into the main body 131 of the atraumatic tip 130, and each of the proximal slots 136a and 136b may extend proximally from the circumferential slot 135. It should be noted that a third proximal slot is not shown in the view of FIG. 3, but would be positioned behind the atraumatic tip 130 in this illustration, such that three proximal slots are disposed about 120 degrees apart relative to one another in this example.

Similarly, one or more distal slots 137, such as slots 137a and 137b, are also recessed slightly into the main body 131 of the atraumatic tip 130, and each of the distal slots 137a and 137b may extend distally from the circumferential slot 135. It should be noted that a third distal slot is not shown in the view of FIG. 3, but would be positioned behind the atraumatic tip 130 in this illustration, such that three distal slots are disposed about 120 degrees apart relative to one another.

The first proximal slot 136a may be disposed at a circumferential position (around the perimeter of the atraumatic tip) that is aligned with the first distal slot 137a, while the second proximal slot 136b may be disposed at another circumferential position that is aligned with the second distal slot 137b (and the third proximal slot would be aligned circumferentially with the third distal slot), as generally depicted in FIG. 3.

Referring to FIG. 4, the delivery system 120 further comprises a radial orientation module 140, which is dimensioned to engage outer regions of the atraumatic tip 130. In particular, the circumferential slot 135 of the atraumatic tip 130 is dimensioned to receive a circumferential base 145 of the radial orientation module 140, as depicted in FIG. 4. Further, the proximal and distal slots 136 and 137 are dimensioned to receive one or more orientation struts 146 that extend outward from the circumferential base 145, as depicted in FIGS. 4 and 5A.

The circumferential slot 135 may be dimensioned such that, when the circumferential base 145 of the radial orientation module is disposed therein, the circumferential base 145 does not extend a significant distance radially outward beyond a maximum diameter of the atraumatic tip 130. In other words, the provision of the circumferential base 145 in the circumferential slot 135 does not significantly increase the overall profile of the atraumatic tip 130 and does not create any uneven regions that could damage the vessel 10 during retrieval of the atraumatic tip 130 after stent-graft deployment. Similarly, the proximal and distal slots 136 and 137 are dimensioned such that, when an orientation strut 146 is disposed therein, the orientation strut 146 does not extend a significant distance radially outward beyond a maximum diameter of the atraumatic tip 130, as depicted in FIG. 4 and FIG. 6.

In one embodiment, the proximal and distal slots 136 and 137 may comprises a generally arcuate shape, as depicted in FIG. 3. The orientation struts 146 may comprise a corresponding arcuate shape, having a first region 147a extending from the circumferential base 145, a second region 147b be extending from the circumferential base 145 at a location radially spaced apart from the first region 147a, and an apex having a curved central region 147c disposed between the first and second regions 147a and 147b, as shown in FIG. 4. It will be appreciated that while generally arcuate shapes are depicted, other shapes and profiles for the orientation struts 146 (and the associated slots in the atraumatic tip) may be provided without departing from the spirit of the present embodiments. However, it is important that the central regions 147c comprise a relatively atraumatic shape, such as a curve of some type, in order to reduce vessel damage or rupture when the orientation struts 146a-146c are in a deployed state.

Referring still to FIG. 4, the delivery system 120 further comprises one or more actuation wires 150, which extend within the lumen 127 of the sleeve 125, i.e., in the space between the sleeve 125 and the cannula 60. In the embodiment of FIGS. 4-6, three actuation wires 150a-150c are provided, where each actuation wire 150a-150c corresponds to an orientation strut 146a-146c, as explained further below.

Each actuation wire 150 comprises a proximal region 152 and a distal region 154, where the distal region 154 extends the distance of the delivery system 120 and may be actuated by a user. Each actuation wire 150 further comprises an engagement region 153, which is disposed at least partially adjacent to a respective orientation strut 146, as depicted in FIGS. 4-6. Each actuation wire 150 is routed, in a distal to proximal direction, such that it extends within the lumen 127 of the sleeve 125, then exits the sleeve 125 and extends radially outward through a distal aperture 139 in the atraumatic tip that is located near the distal end 134 of the atraumatic tip, as shown in FIG. 4. After passing through the distal aperture 139, each actuation wire 150 extends axially along the engagement region 153 and passes over the circumferential base 145 and the respective orientation strut 146, and then enters into a proximal aperture 138 of the atraumatic tip 130. The actuation wire 150 then extends proximally within the atraumatic tip 130, in a space adjacent to the exterior surface 66 of the cannula 60, and terminates at the proximal region 152 as shown in FIG. 4. It should be noted that, although each actuation wire 150 is shown having a separate distal region 154 in FIG. 4, in other embodiments multiple actuation wires 150 may be secured together at a common location, e.g., just distal to the atraumatic tip 130, such that pulling upon a joint actuation wire segment sufficiently retracts all of the engagement regions 153 and proximal regions 152 simultaneously.

During use, the delivery system 120 is inserted into a patient's vessel 10 with the orientation struts 146a-146c in a retracted delivery state with their respective curved central regions 147c extending proximally and substantially flush relative to the exterior surface of the atraumatic tip 130, as depicted in FIG. 4. The delivery system 120 is advanced to a target site in the vessel 10 with the sheath 70 and the stent-graft 80 coupled thereto, as generally explained in FIGS. 1-2. At this time, the orientation struts 146a-146c may be covered by the proximal end 72 of the sheath 70 (as depicted in FIG. 4 with the outer sheath in cross-section), which may be desirable if the orientation struts 146a-146c comprise a shape-memory material with an outward bias. Alternatively, the sheath 70 may be disposed proximal to the orientation struts 146a-146c, which may be held in place sufficiently by the actuation wires 150.

In the embodiment of FIGS. 3-6, when the stent-graft 80 is disposed near a target location in the vessel 10, the sheath 70 may be retracted so as to expose the orientation struts 146a-146c including the circumferential base 145, and the user may actuate the radial orientation mechanism by distally retracting the one or more actuation wires 150, which causes a corresponding actuation of a respective orientation strut 146 from the retracted delivery state of FIG. 4 to an expanded deployed state in FIGS. 5A-5B. In the deployed state, the orientation struts 146 are disposed an angle α relative to one another around a perimeter of the atraumatic tip 130, and the apices or curved regions 147c are spaced a distance away from the atraumatic tip, as depicted from the top view of FIG. 5B. When three orientation struts 146 struts are provided, the angle α may range from about 100 degrees to about 140 degrees, and is preferably about 120 degrees; however, as will be explained below, greater or fewer orientation struts 146 may be provided.

To achieve the corresponding actuation of parts, in one embodiment, each actuation wire 150 may pass through an eyelet 149 in a respective orientation strut 146, as depicted in FIG. 5A. Each actuation wire 150 may comprise a catching member 159 having a slightly larger diameter than other regions of the actuation wire 150, such that the catching member 159 is unable to pass through the eyelet 149 in the orientation strut 146. When the catching member 159 is disposed proximal to the eyelet 149, and cannot pass therethrough, then pulling on the actuation wire 150 in a distal direction will cause the catching member 159 to pull the orientation strut 146 in a corresponding distal direction. By way of example, and without limitation, the catching member 159 may be integrally or externally formed relative to the remainder of the actuation wire 150, and may comprise the shape of a ball, knot, solder or other shapes.

Upon actuation of a respective orientation strut 146 from the retracted delivery state of FIG. 4 to the deployed position of FIGS. 5A-5B, the orientation struts 146 help to orient the atraumatic tip 130 at a relatively central location within the vessel 10, as depicted in FIGS. 2A-2B above. At least, the orientation struts 146 may provide a degree of spacing between the outer surface of the atraumatic tip 130 and the inner wall 12 of the vessel 10.

Advantageously, as explained above with reference to FIGS. 2A-2B, and consistent with the deployed state of FIGS. 5A-5B, due to the spacing of the atraumatic tip 130 from the inner wall 12, when the proximal region 72 of the outer sheath 70 is initially retracted during deployment, then the barbs 96 on the stent 90 will not instantly attach to the inner wall 12 of the vessel 10. Since the barbs 96 refrain from initial engagement with the inner wall 12, then a physician may further orient the graft 81 and/or the stent 90 within the vessel 10. This ability to make additional adjustments of the position of the stent-graft 80, even after the sheath 70 is retracted distally and the barbs 96 are exposed, can significantly improve final positioning and therefore apposition of both the graft 81 and the stent 90 to the inner wall 12 of the vessel 10, which may reduce the occurrence of endoleaks and other adverse events.

As a further advantage, the provision of actuation wires 150 forms an external "grid" to help stabilize the orientation struts 146. As seen in FIGS. 2A-2B and FIG. 5A, the actuation wires 150 extend radially outward beyond an outer perimeter of both the sheath 70 and the atraumatic tip 130 in order to provide better stabilization of the orientation struts 146. In contrast, certain known malecot structures cause a radially outward expansion of wire segments (sometimes referred to as "wings"), but the part that causes the expansion of the wings remains centrally located within a catheter or sheath, and thus there is no supportive grid radially outward to hold the wings in place, as is the case with the radially outward actuation wires 150 that directly support outer central regions 147c of the orientation struts 146.

As yet another advantage, the delivery system 120 provides the ability of the orientation struts 146 to move selectively through a roughly 180 range, i.e., at any desirable angle between the first state of FIG. 4 to the final state of FIG. 6. Specifically, as the actuation wires 150 are distally retracted, the orientations struts 146 will be at different outward diameters, which provides tailoring to needs in a given vessel, e.g., accommodating vessels of different diameters. The outward extension of the orientations struts 146 may also be decided taking into consideration the exterior dimensions of the prosthesis to be deployed. As will be appreciated, the extent of expansion can be determined using radiopaque markers, such as markers 142 of FIG. 5A, which can be positioned on central regions 147c of any of the orientation struts 146a-146c.

Moreover, as yet another advantage, a user may retract one actuation wire 150a-150c to a greater extent than another of the actuation wires 150a-150c, which may move a corresponding orientation strut 146a-146c outward to a greater or lesser extent than other orientation struts 146a-146c. In this manner, the individual orientation struts 146a-146c may be at slightly different radially outward positions, which may provide improved tailoring to a particular vessel anatomy with angulations.

After a procedure is completed, e.g., after the sheath 70 is retracted and the stent-graft 80 has been deployed, an operator may further distally retract the one or more actuation wires 150, which causes a corresponding movement of the respective orientations struts 146 from the position of FIGS. 5A-5B to a retracted withdrawal state shown in FIG. 6. In the state of FIG. 6, the orientation struts 146 may reside within their respective distal slots 137, and be in a position that is substantially flush relative to remainder of the atraumatic tip 130. At this time, an operator may distally retract the delivery system 120 in a relatively safe manner.

Figure 7:
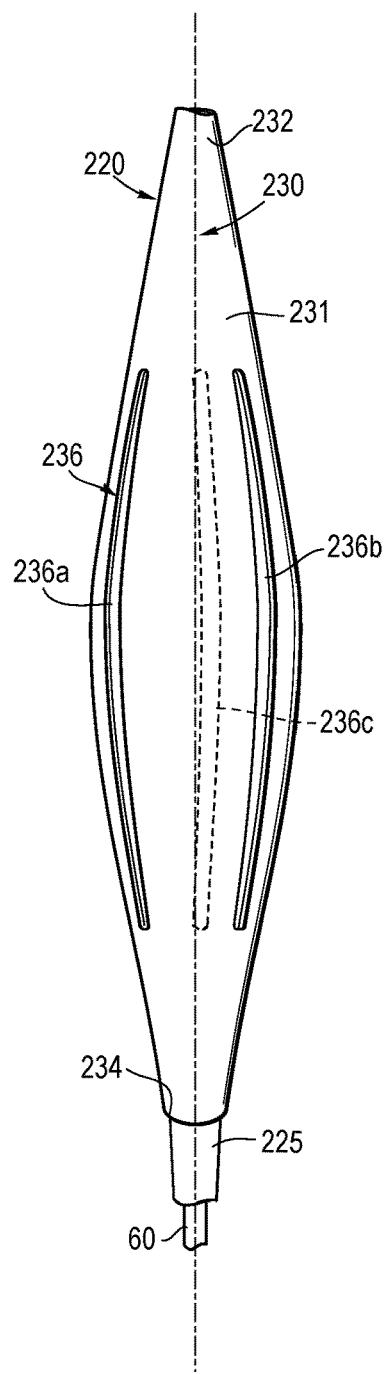
FIG. 7 is a side view of a delivery system having an atraumatic tip according to an alternative embodiment, with orientation struts removed for illustrative purposes.
Figure 8A:
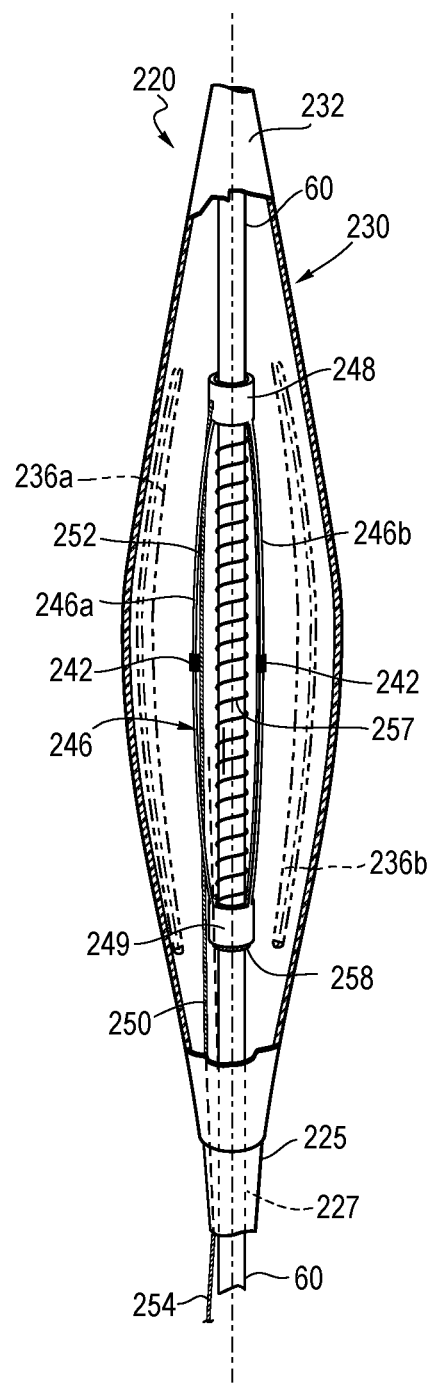
FIGS. 8A-8B are side views of the delivery system of FIG. 7 showing orientation struts in a retracted delivery state within the atraumatic tip, and isolated from the atraumatic tip, respectively.
Figure 8B:
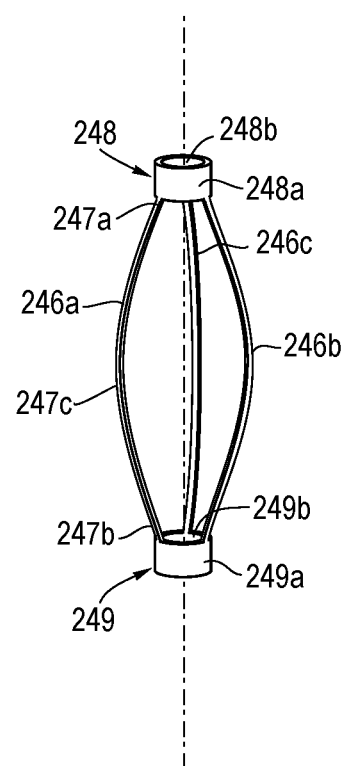
Figure 9:
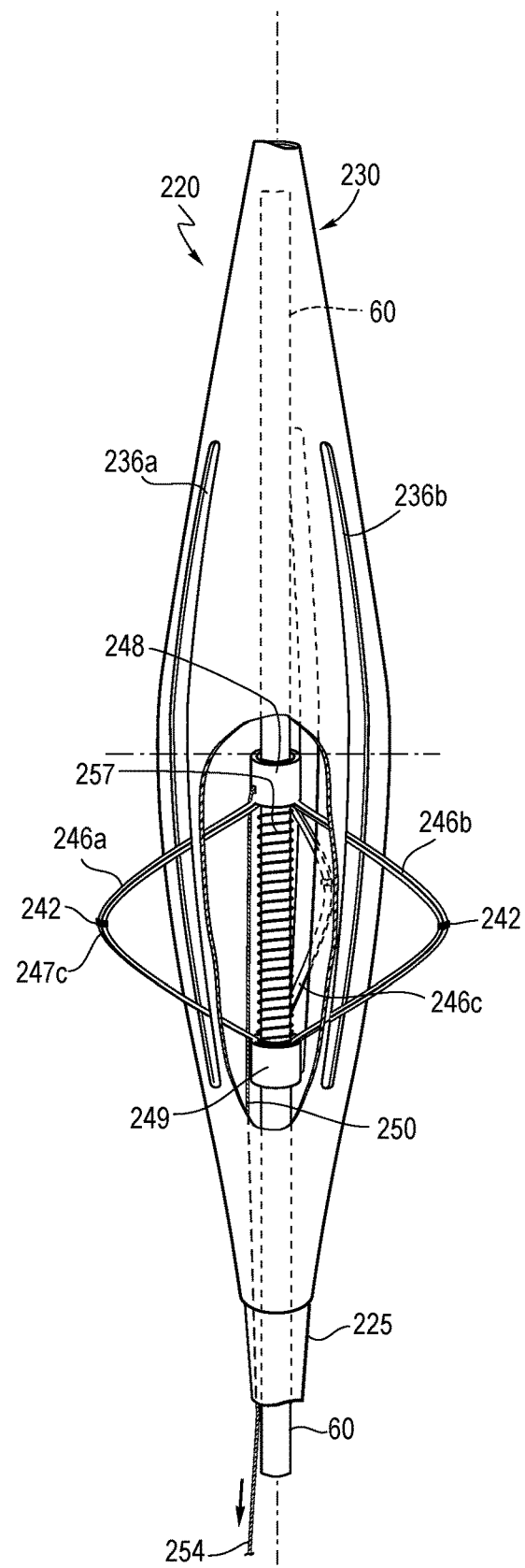
FIG. 9 is a side view of the delivery system of FIGS. 7-8 showing the orientation struts in an expanded deployed state.

Referring now to FIGS. 7-9, an alternative delivery system 220 is shown and described. Operation of the delivery system 220 is similar to operation of the delivery system 120, with notable exceptions explained below. Moreover, like reference numbers are used to designate corresponding parts, e.g., the main body 231 of the atraumatic tip 230 in FIGS. 7-9 will correspond to the main body 131 of the atraumatic tip 130 in FIGS. 3-6.

In the embodiment of FIGS. 7-9, the atraumatic tip 230 comprises one or more axial slots 236, such as slots 236a-236c, which extend through the main body 231 of the atraumatic tip 230, and extend an axial distance while terminating before the proximal end 232 and the distal end 234 of the atraumatic tip 230, as shown in FIG. 7.

Referring to FIGS. 8A-8B, the delivery system 220 further comprises one or more orientation struts 246, such as orientation struts 246a-246c, which are dimensioned to pass through a respective slot 236 in the atraumatic tip 230. As shown in FIG. 8B, each of the orientation struts 246a-246c has a proximal end 247a coupled to a proximal base ring 248, and a distal end 247b coupled to a distal base ring 249. A central region 247c extends between the proximal and distal regions 247a and 247b, and is not directly constrained to a base, thereby being able to move radially outward between the delivery state of FIG. 8A and the deployed state of FIG. 9.

The proximal base ring 248 comprises a main body 248a to which the orientation struts 246 are secured, and a further comprises an aperture 248b having an inner diameter slightly larger than an outer diameter of the cannula 60. Therefore, the proximal base ring 248 is coaxially disposed around the exterior surface of the cannula 60, as shown in FIG. 8A and FIG. 9. The distal base ring 249 comprises a similar main body 249a and aperture 249b, and is disposed around the cannula 60 in a similar manner, as shown in FIG. 8A. An attachment location 258 secures the distal base ring 249 to the cannula 60, e.g., via a solder or weld or mechanical attachment, thereby preventing distal movement of the distal base ring 249 relative to the cannula 60.

As shown in FIG. 8A, an actuation wire 250 extends within a lumen 227 of the sleeve 225, i.e., in the space between the sleeve 225 and the cannula 60. The actuation wire 250 comprises a proximal region 252 and a distal region 254, where the distal region 254 extends the distance of the delivery system 220 and may be actuated by a user. The proximal region 252 of the actuation wire 250 is secured to the proximal base ring 248.

During use, the delivery system 220 is inserted into a patient's vessel 10 in a similar manner as initially described for the delivery system 120, above, with the orientation struts 246a-246c in a substantially elongated position, i.e., where the central regions 247c do not bow radially outward beyond a perimeter of the atraumatic tip 230. A spring 257 may be disposed around the cannula 60, as shown in FIG. 8A, between the proximal and distal base rings 248 and 249, to bias the proximal and distal base rings 248 and 249 axially apart and facilitate a default retracted state of the orientation struts 246.

When the stent-graft 80 is disposed near a target location in the vessel 10, and before the sheath 70 is retracted to expose the stent-graft, the user may actuate the radial orientation mechanism by distally retracting the actuation wire 250 (overcoming the force provided by the spring 257), which causes a corresponding distal movement of the proximal base ring 248 over the cannula 60, as shown in FIG. 9. Since the distal base ring 249 is constrained from distal movement by the attachment location 258, the axial distance between the proximal and distal base rings 248 and 249 is reduced, thereby causing a radial outward movement of the central regions 247c of the orientation struts 246 through the respective slots 236 in the atraumatic tip 230, as seen in FIG. 9. Notably, incremental outward expansion of the central regions 247c may be achieved by varying the extent to which the actuation wire 250 is retracted. Additionally, one or more radiopaque markers 242 may be disposed on each orientation strut 246 near the central region 247c, in order to assist an operator with determining the distance the central region 247c has expanded outward.

In the state of FIG. 9, the delivery system 220 provides spacing of the atraumatic tip 230 from the inner wall 12 of the vessel 10, and achieves many of the advantages explained above with respect to the embodiment of FIGS. 3-6, including but not limited to reducing inadvertent initial engagement of barbs to the vessel wall, improving final positioning of the stent-graft 80 and apposition of both the graft 81 and the stent 90 to the inner wall 12 of the vessel 10, and thereby reducing the occurrence of endoleaks and other adverse events.

After a procedure is completed, e.g., after the sheath 70 is retracted and the stent-graft 80 has been deployed, an operator may release the tension, or distal force, applied upon the actuation wire 250, which allows the spring 257 to push the proximal base ring 248 in a proximal direction to the state of FIG. 8A. This causes a corresponding movement of the respective orientation struts 246 from the expanded position of FIG. 9 to the retracted position shown in FIG. 8A. In the state of FIG. 8A, the orientation struts 246 may reside fully within the atraumatic tip 230. At this time, an operator may distally retract the delivery system 220 in a relatively safe manner.

Figure 10:
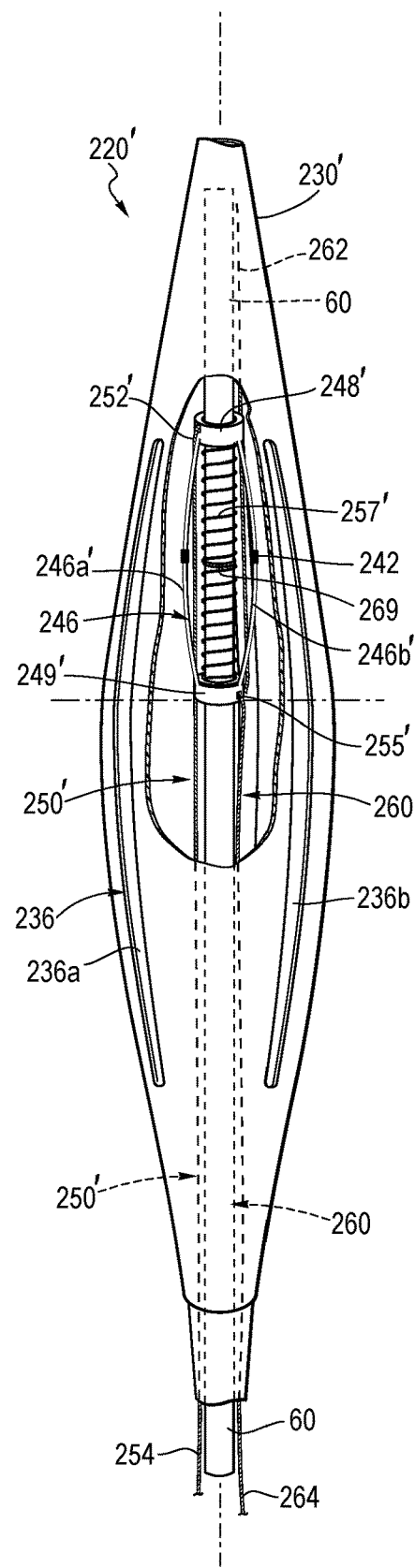
FIGS. 10-12 are, respectively, side views of a delivery system according to a further alternative embodiment with orientation struts in a retracted delivery state, an expanded deployed state, and a retracted withdrawal state.
Figure 11:
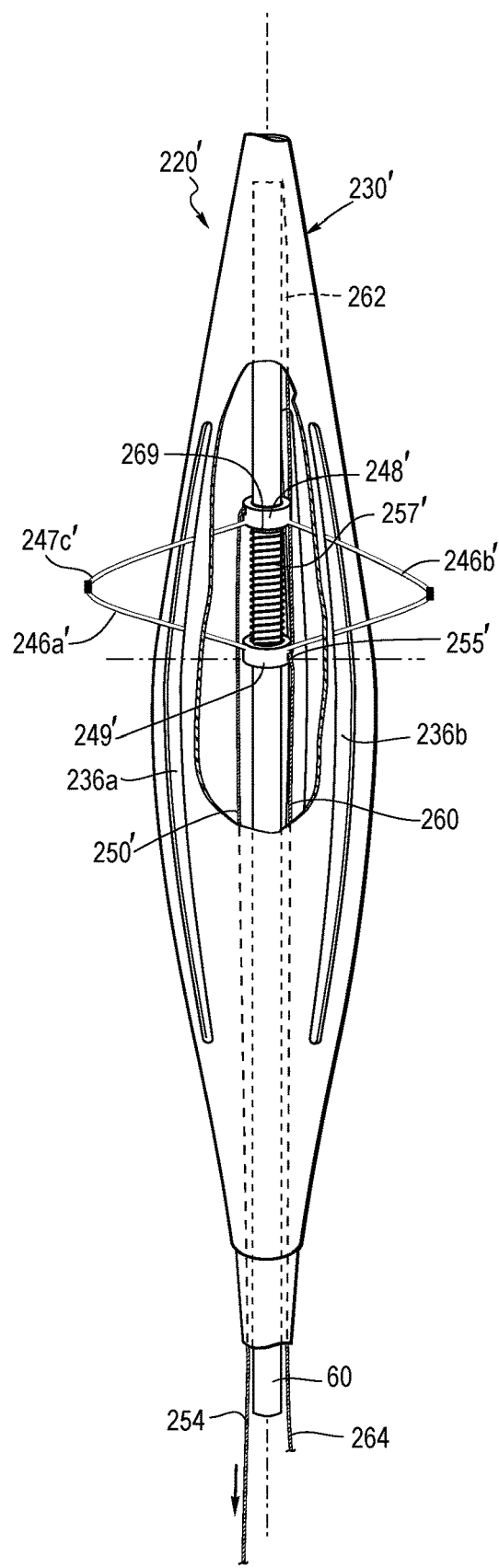
Figure 12:
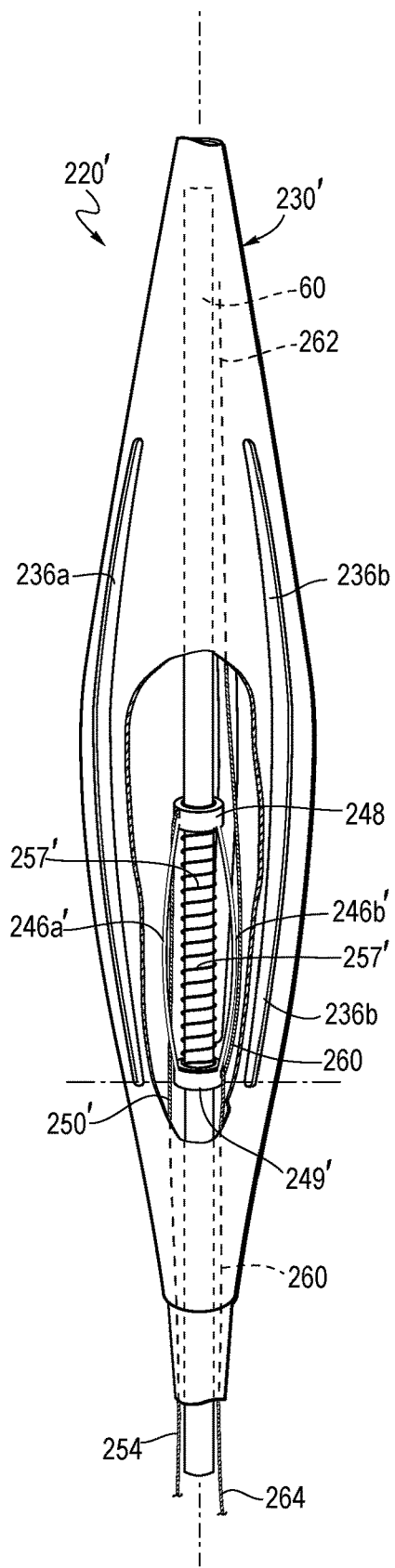

Referring now to FIGS. 10-12, a further alternative delivery system 220' is shown and described, which is similar to the delivery system 220, with notable exceptions detailed below. In this example, the delivery system 220' comprises orientation struts 246' disposed between proximal and distal base rings 248' and 249', in a manner highly similar to FIGS. 7-9, with the exception that the orientation struts 246' may span a shorter axial distance relative the axial slots 236, as shown in FIG. 10.

In FIG. 10, the system 220' comprises first and second actuation wires 250' and 260. The first actuation wire 250' extends from a proximal end 252', where it is secured to the proximal base ring 248', to a distal end 254 for actuation by a user. The second actuation wire 260 is secured to the distal base ring 249' at a location 255', and further extends past the distal and proximal base rings 249' and 248' to a proximal end 262 that is secured within an interior space of the atraumatic tip 230'. The second actuation wire 260 also extends distally to a distal end 264 for actuation by a user, as depicted in FIG. 10.

A stop member 269 is positioned on an exterior surface of the cannula 60, at a location between proximal and distal base rings 248' and 249', as shown in FIG. 10. The stop member 269 is dimensioned such that the proximal and distal base rings 248' and 249' cannot pass axially beyond the stop member 269; however, the spring 257' is dimensioned to be compressed and move around the exterior of the stop member 269.

During use, the delivery system 220' is inserted into a patient's vessel 10 in a similar manner as initially described for the delivery systems 120 and 220, above, with the orientation struts 246a'-246c' in a substantially elongated position, i.e., where the central regions 247c' do not bow radially outward beyond a perimeter of the atraumatic tip 230'. The spring 257' biases the proximal and distal base rings 248' and 249' axially apart and facilitates a default retracted state of the orientation struts 246', as shown in FIG. 10.

When the stent-graft 80 is disposed near a target location in the vessel 10, and before the sheath 70 is retracted to expose the stent-graft, the user may actuate the radial orientation mechanism by distally retracting the first actuation wire 250' (overcoming the force provided by the spring 257'), which causes a corresponding distal movement of the proximal base ring 248' over the cannula 60, as shown in FIG. 11. Retraction of the proximal base ring 248' will be limited by the stop member 269. At this time, the distal base ring 249' may be held steady, and the axial distance between the proximal and distal base rings 248' and 249' is reduced, thereby causing a radial outward movement of the central regions 247c' of the orientation struts 246' through the respective slots 236 in the atraumatic tip 230', as seen in FIG. 11. Notably, incremental outward expansion of the central regions 247c' may be achieved by varying the extent to which the first actuation wire 250' is retracted. One or more radiopaque markers 242 (shown in FIG. 10) may be disposed on each orientation strut 246' near the central region 247c', in order to assist an operator with determining the distance the central region 247c' has expanded outward.

In the state of FIG. 11, the delivery system 220' provides spacing of the atraumatic tip 230' from the inner wall 12, and achieves many of the advantages explained above with respect to the embodiment of FIGS. 3-9, including but not limited to reducing inadvertent initial engagement of barbs to the vessel wall, improving final positioning of the stent-graft 80 and apposition of both the graft 81 and the stent 90 to the inner wall 12 of the vessel 10, and thereby reducing the occurrence of endoleaks and other adverse events.

After a procedure is completed, e.g., after the sheath 70 is retracted and the stent-graft 80 has been deployed, an operator may distally retract the second actuation wire 260, which pulls the distal base ring 249' in a distal direction to the state of FIG. 12. Since the proximal base ring 248' is held longitudinally stationary by the stop member 269, this causes a corresponding movement of the respective orientations struts 246' from the expanded state of FIG. 11 to a retracted withdrawal state shown in FIG. 12. In the state of FIG. 12, the orientation struts 246' may reside fully within the atraumatic tip 230'. At this time, an operator may distally retract the delivery system 220' in a relatively safe manner.

It will be appreciated what while three orientation struts have been depicted in each embodiment above, this is for illustrative purposes only. In other embodiments, greater or fewer than three orientation struts may be provided, e.g., two, four or more orientation struts. The number of slots in the atraumatic tip, and the number of actuation wires, may be adjusted according to the variation in number of orientation struts without departing from the present embodiments.

In any of the embodiments above, the orientation struts may be formed from a suitable material, such as stainless steel or nitinol. If manufactured from nitinol, the orientation struts may be heat set into a desired deployment configuration, as will be appreciated. In the embodiment of FIGS. 7-9 and 10-12, the orientation struts may be formed from a laser cut cannula along with the proximal and distal base rings, or the orientation struts may be externally formed and attached to the proximal and distal base rings. The actuation wires may also be formed of a suitable material, including but not limited to stainless steel and nitinol, and optionally may be coated to reduce friction along selected regions of their length.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A delivery system for facilitating orientation of a prosthesis in a bodily passage, the system comprising:
   an inner cannula having proximal and distal regions;
   an atraumatic tip having a proximal end, a distal end, and a central region disposed therebetween, where at least a portion of the atraumatic tip is coupled to the proximal region of the inner cannula;
   a plurality of orientation struts having a retracted delivery state, an expanded deployed state, and a retracted withdrawal state,
   wherein each of the plurality of orientation struts has an apex that is oriented proximally relative to the atraumatic tip in the retracted delivery state, is oriented radially outward relative to the atraumatic tip in the expanded deployed state, and is oriented distally relative to the atraumatic tip in the retracted withdrawal state.

2. The system of claim 1, wherein the apex of each of the plurality of orientation struts travels a distance of between about 150 degrees and about 210 degrees from the retracted delivery state to the retracted withdrawal state.

3. The system of claim 1, further comprising a proximal slot disposed in an exterior surface of the atraumatic tip and dimensioned to house a first orientation strut in the retracted delivery state, and a distal slot disposed in an exterior surface of the atraumatic tip and dimensioned to house the first orientation strut in the retracted withdrawal state.

4. The system of claim 3, wherein each of the first orientation strut, the proximal slot, and the distal slot comprises an arcuate shape.

5. The system of claim 1, further comprising a circumferential base extending around a perimeter of the atraumatic tip, wherein each of the plurality of orientation struts is coupled to the circumferential base.

6. The system of claim 5, further comprising a circumferential slot disposed in an exterior surface of the atraumatic tip, wherein the circumferential slot is dimensioned to house the circumferential base.

7. The system of claim 1, wherein the plurality of orientation struts comprises three orientation struts that are circumferentially spaced apart relative to one another between about 100 degrees and about 140 degrees.

8. The system of claim 1, further comprising a plurality of actuation wires, where each actuation wire comprises proximal and distal regions,
   where a first actuation wire of the plurality of actuation wires causes movement of a first orientation strut from the retracted delivery state, to the expanded deployed state, and to the retracted withdrawal state of the first orientation strut, and
   where a second actuation wire of the plurality of actuation wires causes movement of a second orientation strut from the retracted delivery state, to the expanded deployed state, and to the retracted withdrawal state of the second orientation strut.

9. The system of claim 8, wherein the first and second actuation wires are capable of independent retraction relative to one another along their lengths, such that the first and second orientation struts may be actuated independently at different times.

10. The system of claim 8, wherein the first actuation wire is coupled to the first orientation strut adjacent to the apex at a central region of the first orientation strut.

11. The system of claim 10, wherein the central region of the first orientation strut comprises an eyelet, and a catching member is coupled to the first actuation wire at a location proximal to the eyelet, where the catching member comprises an outer diameter larger than an inner diameter of the eyelet, such that distal retraction of the first actuation wire causes the catching member to pull the first orientation strut in a distal direction.

12. The system of claim 8, further comprising a sleeve disposed coaxially around the cannula, where portions of the first and second actuation wires extend through a lumen of the sleeve.

13. The system of claim 12, further comprising proximal and distal apertures in the atraumatic tip, where the first actuation wire extends from the sleeve in a direction outwardly through the distal aperture, then extends around the first orientation strut, and then extends inwardly through the proximal aperture.

14. A delivery system for facilitating orientation of a prosthesis in a bodily passage, the system comprising:
- an inner cannula having proximal and distal regions;
- an atraumatic tip having a proximal end, a distal end, and a central region disposed therebetween, where at least a portion of the atraumatic tip is coupled to the proximal region of the inner cannula;
- a plurality of orientation struts having a retracted delivery state, an expanded deployed state, and a retracted withdrawal state; and
- a plurality of actuation wires, where each actuation wire comprises proximal and distal regions,
- where a first actuation wire of the plurality of actuation wires causes movement of a first orientation strut from the retracted delivery state, to the expanded deployed state, and to the retracted withdrawal state of the first orientation strut,
- where a second actuation wire of the plurality of actuation wires causes movement of a second orientation strut from the retracted delivery state, to the expanded deployed state, and to the retracted withdrawal state of the second orientation strut, and
- wherein the first and second actuation wires are capable of independent retraction relative to one another along their lengths, such that the first and second orientation struts are actuated independently at different times.

15. The system of claim 14, further comprising a circumferential base extending around a perimeter of the atraumatic tip, wherein each of the plurality of orientation struts is coupled to the circumferential base.

16. The system of claim 14, wherein the first actuation wire is coupled to the first orientation strut at a central region of the first orientation strut, wherein the central region of the first orientation strut extends away from the atraumatic tip in the expanded deployed state.

* * * * *